United States Patent [19]

Kraus

[11] Patent Number: 5,656,425
[45] Date of Patent: Aug. 12, 1997

[54] SCREENING FOR MUTATIONS BY EXPRESSING CDNA SEGMENTS

[75] Inventor: Jan P. Kraus, Littleton, Colo.

[73] Assignee: Regents of the University of Colorado, Boulder, Colo.

[21] Appl. No.: 108,216

[22] Filed: Aug. 17, 1993

[51] Int. Cl.⁶ .............................. C12Q 1/68; C12P 21/00
[52] U.S. Cl. .................. 435/6; 435/69.1; 935/77; 935/78
[58] Field of Search .................. 435/6, 91.41, 91.42, 435/69.1, 320.1

[56] References Cited

U.S. PATENT DOCUMENTS 4,935,341  6/1990  Bargmann et al. .................. 435/6

OTHER PUBLICATIONS

Kozich et al. (Aug. 18, 1992) Human Mutation 1: 113–123.
Franchis et al. (1994) Human Molecular Genetics 3(7): 1103–1108.
Matsuura et al. Hum. Genet (1994) 93: 129–134.
Kozich et al. Am. J. Hum. Genet (1994) 49 (4 Suppl.): 410.

*Primary Examiner*—Lisa B. Arthur
*Attorney, Agent, or Firm*—Frederick W. Pepper

[57] ABSTRACT

A rapid screening method is described for detecting, localizing, and expressing pathogenic mutations in patients suffering from diseases which can include genetically inherited diseases. The screening method allows simultaneous localization and expression of the mutation. By identifying the types and locations of the mutations causing a disease, the method can aid in determining the course of treatment for the disease. The method involves making an expression vector containing a sequence encoding an inactive enzyme by deleting a segment of the coding sequence of the enzyme in the vector, replacing the deleted segment with a corresponding segment from a patient's enzyme coding sequence to make a hybrid enzyme, expressing the hybrid enzyme and assaying the hybrid enzyme for activity to determine whether the Patient's enzyme cDNA contains a pathogenic mutation.

10 Claims, 10 Drawing Sheets

SCREENING FOR MUTATIONS BY EXPRESSING CDNA SEGMENTS

The U.S. Government has a paid-up license in this invention and the right in limited circumstances to require the patent owner to license others on reasonable terms as provided for by the terms of Grant No. P01 HD08315 awarded by the National Institute of Child Health and Human Development.

FIELD OF THE INVENTION

The present invention relates to a method for detecting, localizing, and expressing pathogenic mutations in genes of patients suffering from different diseases which include genetically inherited diseases. More specifically, the invention relates to a method for detecting, localizing, and expressing a pathogenic mutation in the cystathionine β-synthase gene of a patient suffering from homocystinuria.

BACKGROUND OF THE INVENTION

The common approach to identification of disease causing mutations usually involves screening at a level of genomic DNA or cDNA. There are several methods which can detect single base substitutions in a single or double stranded DNA segment. These include RNAse sensitivity assay [Myers et al., Science 230:1242–1246 (1985)], denaturing gradient gel electrophoresis [Myers et al., Nature 313:495–498 (1985)], chemical cleavage at mismatches [Cotton et al., Proc Natl Acad Sci USA 85:4397–4401 (1988)] and, finally, single strand conformation polymorphism analysis [Orita et al., Genomics 5:874–879 (1989)]. Once the aberrant fragment is identified, the mutation is verified by sequencing. These methods detect both the pathogenic mutations as well as the normally occurring polymorphisms. Eventually, the detected changes need to be tested for pathogenicity by expression in E. coli [Gregersen et al, Hum Genet 86:545–551 (1991)] or mammalian cells [e.g., Reichardt et al., Genomics 12:596–600 (1992)]. These methods do not distinguish between nonpathogenic and pathogenic mutations or allow simultaneous localization and expression of the mutation. Therefore, such screening methods require weeks of effort before the pathogenic mutation can be identified. What is needed is a rapid screening method that allows simultaneous localization and expression of the pathogenic mutation.

Cystathionine β-synthase (CBS) [L-serine hydrolyase (adding homocysteine); EC 4.2.1.22], a pyridoxal 5'-phosphate (PLP) dependent enzyme, plays a key role in the transsulfuration of homocysteine in eukaryotes [Mudd et al., The Metabolic Basis of Inherited Disease, 6th ed., pp 693–734, McGraw-Hill, New York (1989)]. Under physiological circumstances, about half of the intracellular homocysteine is transsulfurated yielding cysteine. The remainder is remethylated to methionine in the methionine cycle [Finkelstein and Martin, J Biol Chem 259:9508–9513 (1984)]. S-Adenosyl-L-methionine (AdoMet) regulates homocysteine flux through these branches. At low levels of AdoMet, remethylation of homocysteine is unimpaired. Elevated levels, on the other hand, inhibit remethylation pathways and increase the irreversible transsulfuration by stimulating CBS [Kutzbach and Stockstad, Biochim Biophys Acta 250:459–477 (1971); Finkelstein and Martin, Biochem Biophys Res Commun 118:14–19 (1984); Finkelstein et al., Biochem Biophys Res Commun 66:81–87 (1975)].

Deficiency of CBS is the leading cause of homocystinuria (HCS) in humans. The symptoms and signs of this condition are well characterized. They include dislocated optic lenses, skeletal disorders, mental retardation, and often fatal thromboembolism [Mudd et al., The Metabolic Basis of Inherited Disease, 6th ed., pp 693–734, McGraw-Hill, New York (1989)]. Transsulfuration is blocked, resulting in the accumulation of homocyst(e)ine and often methionine together with depletion of cysteine and cystathionine in body fluids. In about half of the affected patients, these symptoms can be alleviated by pyridoxine administration. The rationale for this treatment is based, in part, on the observation that some of the mutant CBS proteins bind pyridoxal 5'-phosphate less avidly than normal [Lipson et al., J Clin Invest 66:188–193 (1980) ].

Normal CBS is a homotetramer of 63 kDa subunits [Skovby et al., J Biol Chem 259:583–593 (1984)]; its gene resides on human chromosome 21 at q22.3 [Skovby et al., Hum Genet 65:291–294 (1984); Münke et al., Am J Hum Genet 42:550–559 (1988)]. It has been shown that CBS mutations do not usually alter the subunit size; however, the intracellular CBS concentrations are generally markedly reduced [Skovby et al., Am J Hum Genet 36:452–459 (1984)]. These studies suggest that the majority of the synthase genetic defects are missense rather than nonsense mutations or internal deletions. None of these mutations has been examined at the molecular level. To facilitate these studies of CBS mutations, a rapid screening method for pathogenic mutations was developed incorporating either a prokaryotic or eukaryotic expression system. Such an expression screening system has wide applicability in detecting and localizing pathogenic mutations involved in diseases which include genetically inherited diseases. Some examples of genetically inherited diseases include glutaric acidemia type I caused by a deficiency of glutaryl-CoA dehydrogenase, glutaric acidemia type II caused by a deficiency of ETF dehydrogenase, acyl-CoA dehydrogenase medium chain deficiency, propionic acidemia caused by a deficiency of propionyl-CoA carboxylase, Sandhoff's disease characterized by a defect in the production of hexosaminidases A and B, citrullinemia which is a disease of the amino acid metabolism caused by a deficency in argininosuccinic acid synthetase, and Fabry's disease, an X-linked recessive disorder due to deficiency of α-galactosidase.

SUMMARY OF THE INVENTION

One embodiment of the invention is a screening method for locating the position of a pathogenic mutation in an enzyme gene. This involves screening for subregions of the cDNA coding region of an enzyme gene of human patient suffering from a disease which can be a genetically inherited disease. This is accomplished by the expression of hybrid cDNAs of the enzyme gene in a prokaryotic or eukaryotic system. The hybrid cDNAs consist of subregions derived from the patient's cDNA in the context of an otherwise normal sequence of the expression vector. Absence of the enzyme activity or lower than normal enzyme activity is considered as a marker for pathogenic mutations within the investigated cDNA subregion. A preferred embodiment of the invention uses a prokaryotic expression system such as E. coli. Using such a system allows sequencing of the affected DNA region within a week after the patient's cells have been harvested from tissue culture. In screening for the cystathionine β-synthase gene, this method allows for both the separation of parental alleles and preliminary localization of the pathogenic mutation site(s).

To eliminate false positive results from uncut expression vectors in screening for pathogenic mutations, the above embodiment is modified. In the modified screening expression system, expression vectors are introduced carrying a segment deletion in the subregions of the cDNA coding region corresponding to the subregions to be inserted from the patients' cDNA. The segment deletion results in an inactive enzyme produced from the starting expression vectors. This modified screening expression system also allows colonies of expression vectors to be screened by PCR to confirm the presence of the patient's cDNA insert. This screening is based on the difference in size of the patient's cDNA insert from the corresponding subregion of the starting expression vector.

Another embodiment is a screening method for a pathogenic mutation in the allele of a heterozygous individual. The alleles are separated into different expression vectors. The screening is carried out using full length cDNAs from a patient rather than the subregions of his cDNA. In this embodiment of the invention, the screening method detects whether an allele carries a pathogenic mutation rather than locating the position of the pathogenic mutation on the cDNA. Separation of the parental alleles into different expression vectors and identifying each allele by using a polymorphic marker further allows the examination of the putative assocation of heterozygous deficiency and genetically inherited diseases. A specific example for examination is the association of heterozygous cystathionine β-synthase deficiency and premature occlusive arterial disease [Ueland and Refsum, *J Lab Clin Med* 114:473–501 (1989); Malinow, *Circulation* 81:2004–2006 (1990); Clarke et al., *N Engl J Med* 324:1149–1155 (1991)].

A futher embodiment is a screening method that separates alleles in an individual and identifies a protein encoded by an allele. The alleles of the individual are separated into different expression vectors. After using a polymorphic marker to identify each allele, a protein encoded by the allele is expressed and then identified by detecting means such as chromatography, electrophoresis, and immunological methods.

DETAILED DESCRIPTION OF THE INVENTION

Figure 1:
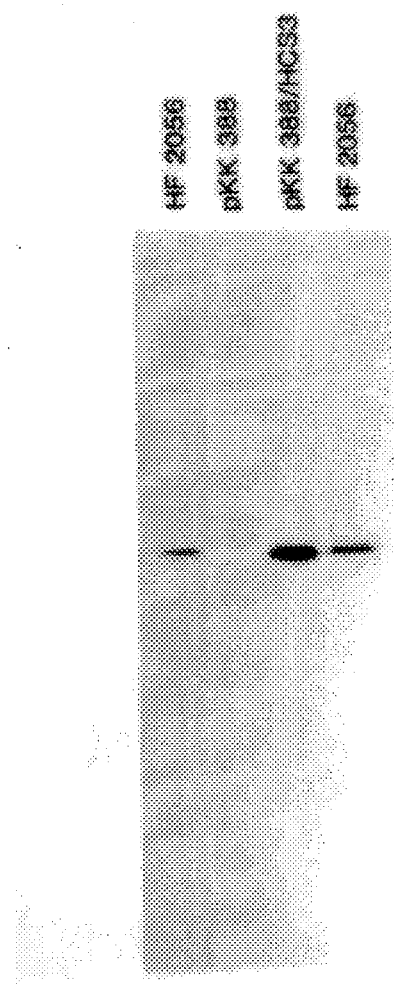
FIG. 1 represents a Western analysis of normal human CBS expressed in *E. coli*.

The present invention relates to a screening method for pathogenic mutations and allows simultaneous localization and expresion of the mutations. The present invention effectively separates the two alleles in patients with diseases, which include genetically inherited diseases, into different expression vectors.

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA. Clearly, a lack of replication would render them effectively inoperable. In sum, "expression vector" is also given a functional definition. Generally, expression vectors of utility in DNA recombinant techniques are often in the form of "plasmids". Plasmids refer to either circular double stranded DNA molecules or circular single stranded DNA molecules, containing an origin of replication derived from a filamentous bacteriophage. These DNA molecules, in their vector form, are not linked to the chromosomes. Other effective vectors commonly used are phage and non-circular DNA. In the present specification, "plasmid" and "vector" are often used interchangeably. However, the invention is intended to include such other forms of expression vectors which serve equivalent functions and which are, or subsequently become, known.

Recombinant vectors and methodology disclosed herein are suitable for use in prokaryotic and eukaryotic expression systems. These expression systems include microbial strains, such as *E. coli* and *Saccharomyces cerevisiae*.

In locating the position of a pathogenic mutation in an enzyme gene of a human patient suffering from a disease, which can be a genetically inherited disease, the method comprises:

(a) replacing at least one subregion of a coding region of a normal enzyme cDNA in an expression vector with at least one inserted corresponding subregion of a coding region of an enzyme cDNA from the patient;

(b) generating a hybrid enzyme from an expression system, wherein the hybrid enzyme contains a portion encoded by at least one inserted subregion of the patient cDNA;

(c) assaying the hybrid enzyme for activity, an absence of enzyme activity or lower than normal enzyme activity indicating the presence of the pathogenic mutation in the inserted subregion of the patient cDNA;

(d) sequencing the inserted subregion of the patient cDNA in the total cDNA of the hybrid enzyme lacking activity or have lower than normal activity; and (e) comparing the inserted subregion of the patient cDNA with the corresponding subregion of the normal cDNA or the normal genomic DNA to locate the position of the pathogenic mutation.

In locating the position of a pathogenic mutation in an enzyme gene of a human patient suffering from a disease, which can be a genetically inherited disease, the method further comprises:

identifying each enzyme allele in the expression vector by detecting a polymorphic marker for the allele wherein use of a polymorphic marker can distinguish between enzyme alleles when each allele has a different nucleotide triplet mutation that codes for the same amino acid change.

In locating the position of a pathogenic mutation in an enzyme gene of a human patient suffering from a disease, which can be a genetically inherited disease, without false positive results from uncut expression vectors containing the complete normal enzyme cDNA coding region, the method comprises:

(a) deleting at least one segment of a coding region of a normal enzyme cDNA in a starting expression vector to produce an inactive enzyme, wherein the segment deletion is from a subregion of the coding region of the normal cDNA corresponding to a subregion of a coding region of an enzyme cDNA from the patient;

(b) replacing in the starting expression vector the subregion of the normal cDNA having undergone segment deletion with the inserted corresponding subregion of the patient cDNA;

(c) generating a hybrid enzyme from an expression system, wherein the hybrid enzyme contains a portion encoded by at least one inserted subregion of the patient cDNA;

(d) assaying the hybrid enzyme for activity, an absence of enzyme activity or lower than normal enzyme activity indicating the presence of the pathogenic mutation in the inserted subregion of the patient cDNA;

(e) sequencing the inserted subregion of the patient cDNA in the total cDNA of the hybrid enzyme lacking activity or having lower than normal activity; and (f) comparing the inserted subregion of the patient cDNA with the corresponding subregion of the normal cDNA or normal genomic DNA to locate the position of the pathogenic mutation.

In locating a pathogenic mutation without false positive results from uncut expression vectors, the method above further comprises:

screening of expression vectors from step (b) by PCR to confirm the presence of the patient's cDNA insert by comparing the difference in size of the patient's cDNA insert to a corresponding coding subregion having undergone segment deletion in the starting expression vector.

In locating a pathogenic mutation without false positive results from uncut expression vectors, the method above further comprises:

identifying each enzyme allele in the expression vector by detecting a polymorphic marker for the allele wherein use of a polymorphic marker can distinguish between enzyme alleles when each allele has a different nucleotide triplet mutation that codes for the same amino acid change.

In detecting a pathogenic mutation in an enzyme allele of a heterozygous individual, the method comprises:

(a) separating the enzyme alleles of the individual by subcloning PCR amplified enzyme cDNAs into an expression vector;

(b) identifying each allele in the expression vector by detecting a polymorphic marker for the allele;

(c) generating an enzyme encoded by the allele from an expression system; and (d) assaying the enzyme for activity, an absence of enzyme activity or lower than normal enzyme activity indicating the presence of the pathogenic mutation in the enzyme allele.

In separating alleles in an individual and identifying a protein encoded by an allele, the method comprises:

(a) separating the alleles of the individual by subcloning PCR amplified cDNAs into an expression vector;

(b) isolating the allele in the expression vector by detecting a polymorphic marker for the allele;

(c) generating a protein from an expression system; and (d) identifying the protein by detecting means such as chromatography, electrophoresis, and immunological methods.

Method for Locating the Position of a Pathogenic Mutation

A. Properties of Human CBS in *E. coli* Lysates

Bacteria transformed with the wild-type human cDNA construct pHCS3 express CBS. The size (63 kDa) of its subunits is indistinguishable from normal human fibroblast CBS subunits as shown in the Western analysis of normal human CBS expressed in *E. coli* (FIG. 1). The Lanes depicted in FIG. 1 are the following: HF 2056, human fibroblast extract containing 336 μg protein and 9.2 U of CBS; pKK 388, *E. coli* lysate from cells harboring the parent pKK388.1 plasmid, 156 μg protein, 0 units; pKK/HCS3, *E. coli* lysates from cells containing the CBS expression plasmid, pHCS3, 156 ug of protein, 6 U of CBS. The expression product reacts with both antihuman and antirat CBS antibodies. The enzymatic activity of normal human CBS in the *E. coli* lysates was comparable to that of human liver (200 U/mg protein) (Kraus and Rosenberg, 1983).

B. Functional Screen for Mutations in a Homocystinuric Individual

Figure 2:
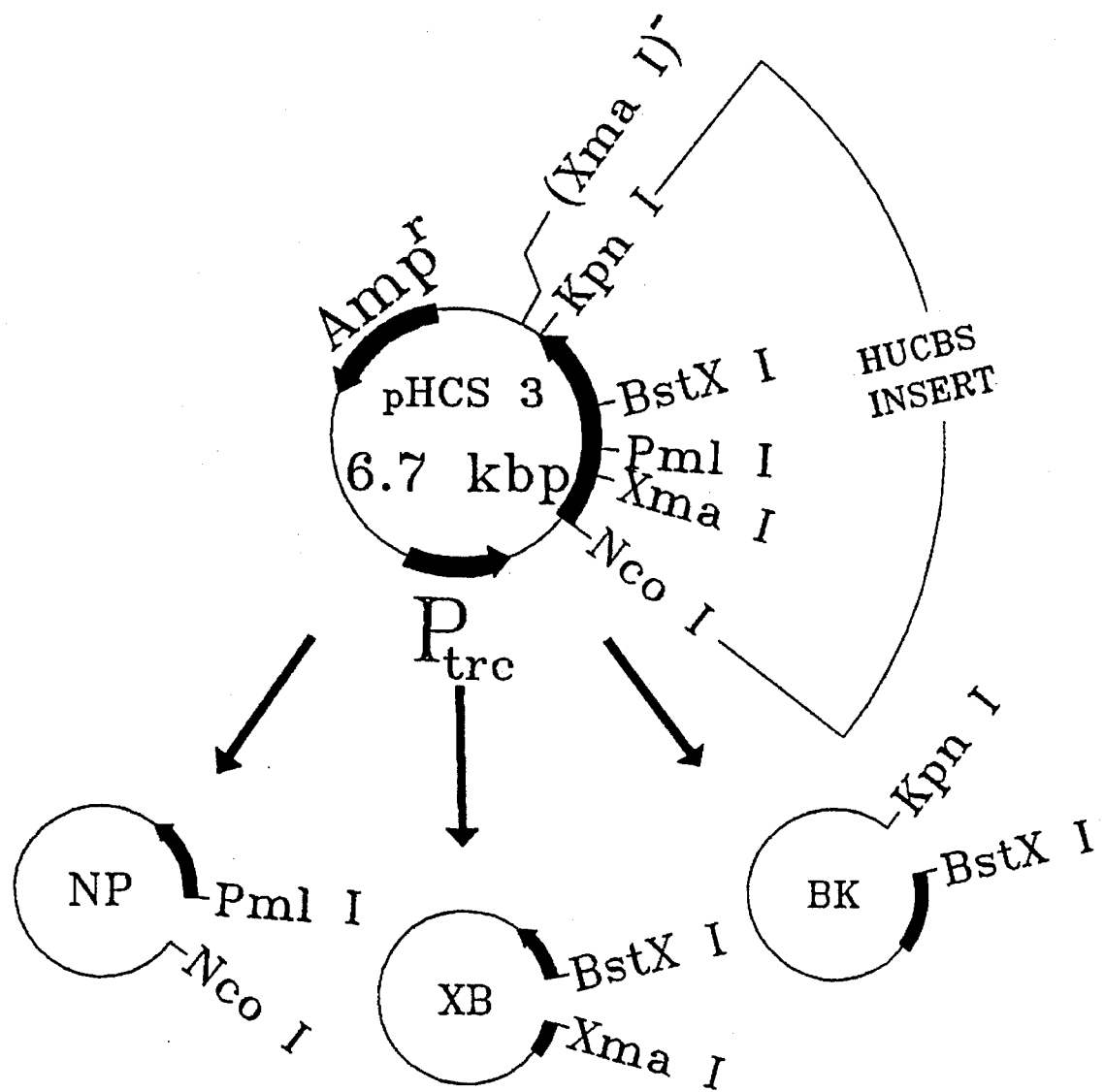
FIG. 2 is a schematic representing the expression plasmid pHCS3 and derived cartridges.
Figure 3:
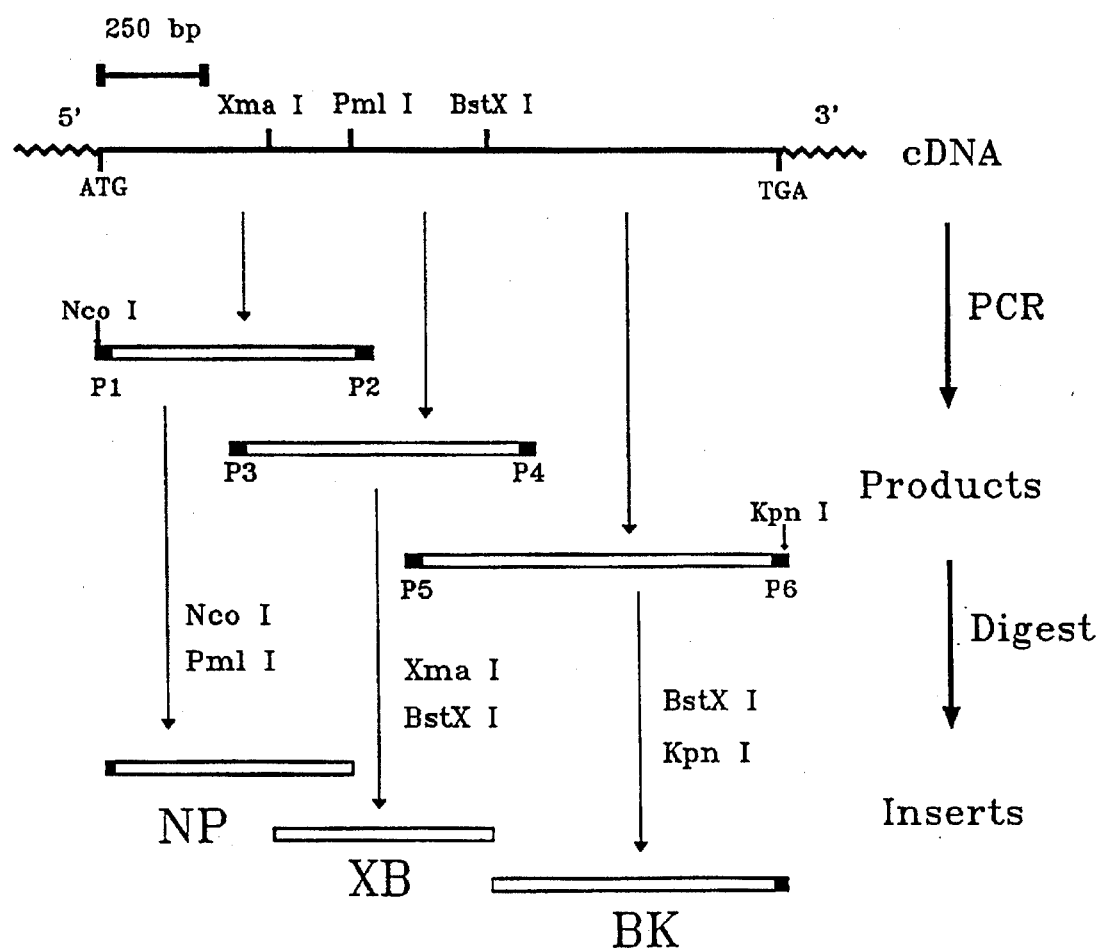
FIG. 3 is a schematic representing the preparation of CBS inserts.

In order to find the pathogenic mutations in the patient's CBS, three PCR amplified segments of the coding region of his cDNA were used to replace the corresponding segments of the normal sequence in pHCS3 expression cartridges, as shown in FIG. 2. NP insert represented nts 31–609, XB and BK inserts corresponded to nts 413–942 and 943–1646, respectively, of the patient cDNA (FIG. 3). PCR of NP and XB segments yielded products of the expected lengths, however PCR of BK segment yielded two fragments, one ~130 bp shorter and about 5-fold more abundant than normal.

C. Absence of a Segment Activity as an Indication of Mutation

Hybrid human CBS, containing portions encoded by patient's cDNA, was expressed in *E. coli*. Typically 8 individual colonies as well as pools of as many as 400 colonies were assayed. Clones harboring the patient's NP segment exhibited normal CBS activity both in individual colonies (7 of 8 clones) as well as in the pool of colonies (98% of control activity), as shown in Table 1 below.

TABLE 1

CBS Activities of Hybrid Protein Expressed in *E. coli*[a]

| Segment inserted[b] | Fraction of colonies with CBS activity | Mixed culture % control activity | Deduced segment zygosity[c] |
|---|---|---|---|
| NP | 7/8 | 98 | AA |
| XB | 3/7 | 40 | $Aa_2$ |
| BK | 4/18 | 29 | $Aa_1$ |

[a]Hybrid CBS containing different portions of patient's CBS cDNA was expressed and assayed in single colonies lysates. Mixed cultures were expressed after combining the individual colonies from the agar plate and assayed as described.
[b]Abbreviations in this column refer to cDNA inserts restricted with the following enzyme pairs: NP, Nco I/Pml I; XB, Xma I/Bst XI; BK, Bst XI/Kpn I.
[c]Segment zygosity: A, normal allele; $a_1$, defective paternal allele; $a_2$, defective maternal allele.

On the other hand, about half of the colonies (3 of 7), containing the XB segment, had CBS activity. This observation corresponds well with the depressed activity (40%) when a mixture of these transformants was compared with the control. Expression of the patient's BK segment yielded 4 individual clones with activity out of 18 and the mixture of colonies had 29% activity of the control. The higher fraction of clones with inactive CBS was most probably due to the greater abundance of the shorter PCR product.

From these data it can be concluded that the patient was compound heterozygous for pathogenic mutations in the middle (XB) and the 3'-coding (BK) regions of the cDNA. Subsequently, DNA prepared from the individual inactive colonies as well as from the pools of colonies was sequenced.

D. DNA Sequencing of the Affected Regions

Figure 4A:
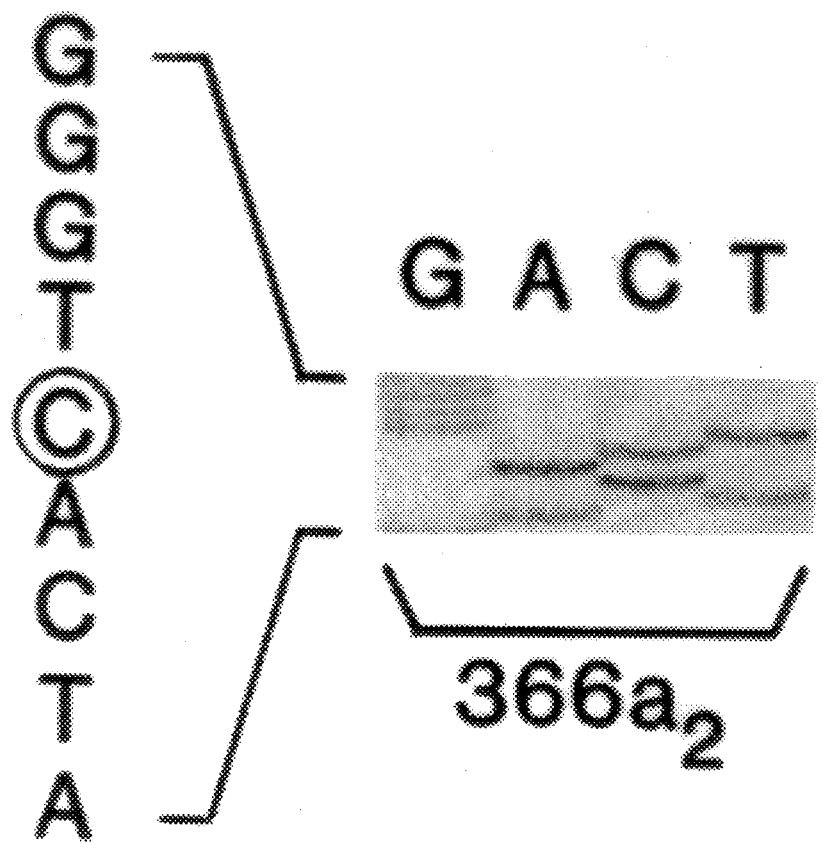
FIG. 4A represents a DNA sequence of PCR-amplified cDNA from patient 366 showing a pathogenic mutation.

DNA sequences of two individual XB clones without CBS activity revealed the first pathogenic mutation. The only mutation detected in these colonies was a $T_{833} \rightarrow C$ transition causing a I278T amino acid change. This mutation creates a new BsrI restriction site. Both strands of plasmid DNA from a single bacterial colony harboring an enzymatically deficient pHCS3 /XB segment were sequenced from positions 630 to 940. Nucleotides 829 to 837 of the sense strand are shown in FIG. 4A, the abnormal C in position 833 in place of a normal T is indicated by the Ⓒ. Two clones with normal CBS activity were also sequenced and only the wild type XB sequence was observed. Sequencing of the mixture of colonies yielded nucleotides T and C at the position 833 in equal amounts. This finding is consistent with patient's heterozygosity for this mutation. In addition, a synonymous polymorphism (Y233Y) at position 699 (C→T) was observed both in clones with and without CBS activity.

Figure 4B:
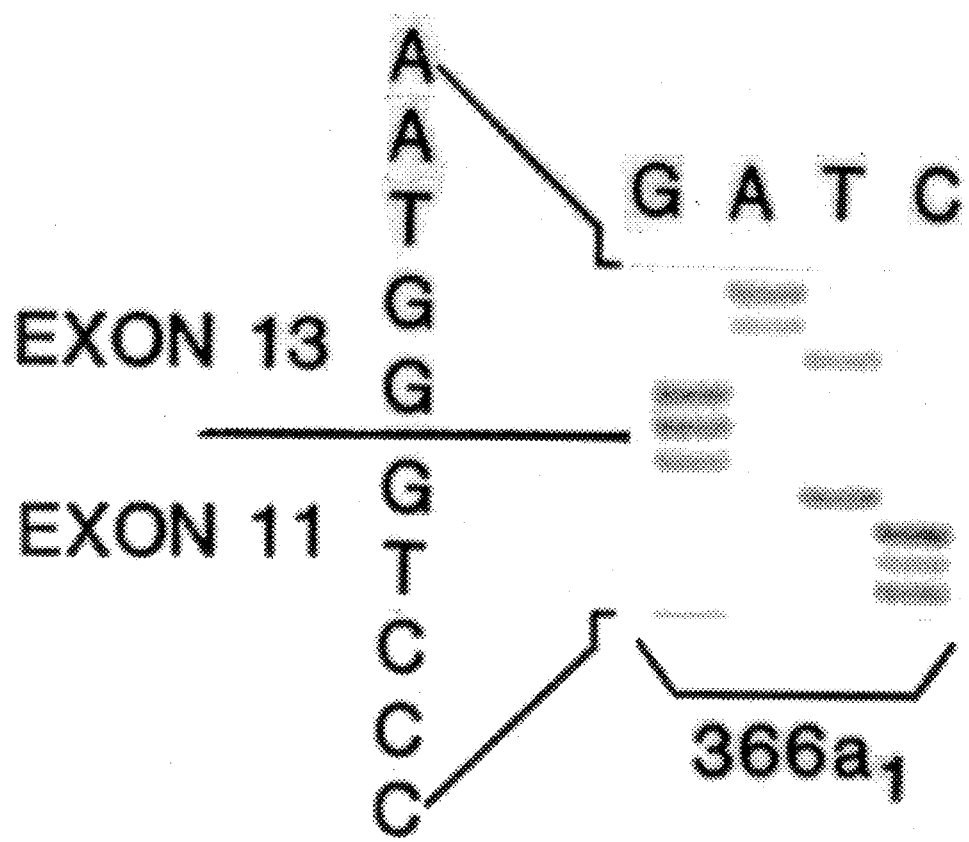
FIG. 4B represents a DNA sequence of PCR-amplified cDNA from patient 366 showing a pathogenic mutation.

The sequence of the inactive BK clones (n=3) revealed the presence of a 135 bp deletion (position 1224–1358 bp) (FIG. 4B) which resulted in a 45 amino acid residue in-frame deletion (W408 to G453). This deletion corresponds to exon 12 of the rat CBS gene [Swaroop et al., *J Biol Chem* 267:11455–11461 (1992)] and indicates a splicing error due to a mutation in intron 11 or 12 as a primary cause for the exon deletion. Both strands of plasmid DNA from a single bacterial colony harboring the 135 base pair shorter, enzymatically deficient pHCS3 /BK segment were sequenced. The sequence derived from the junction of exon 11 and exon 13 is shown in FIG. 4B, indicating the absence of exon 12.

E. Mutation Analysis in the Patient's Parents

The maternal origin of the $T_{833} \rightarrow C$ transition was verified by subcloning, expressing and sequencing the mother's cDNA. Two clones harboring NcoI-BstXI portion of her cDNA contained the mutation $T_{833} \rightarrow C$ (FIG. 5A) which was previously demonstrated in the patient. The expression experiment was consistent with heterozygosity (4 nonexpressing clones out of 8 assayed). It can be concluded from the data that the $T_{833} \rightarrow C$ transition is the maternally inherited mutation in the patient.

Figure 5A:
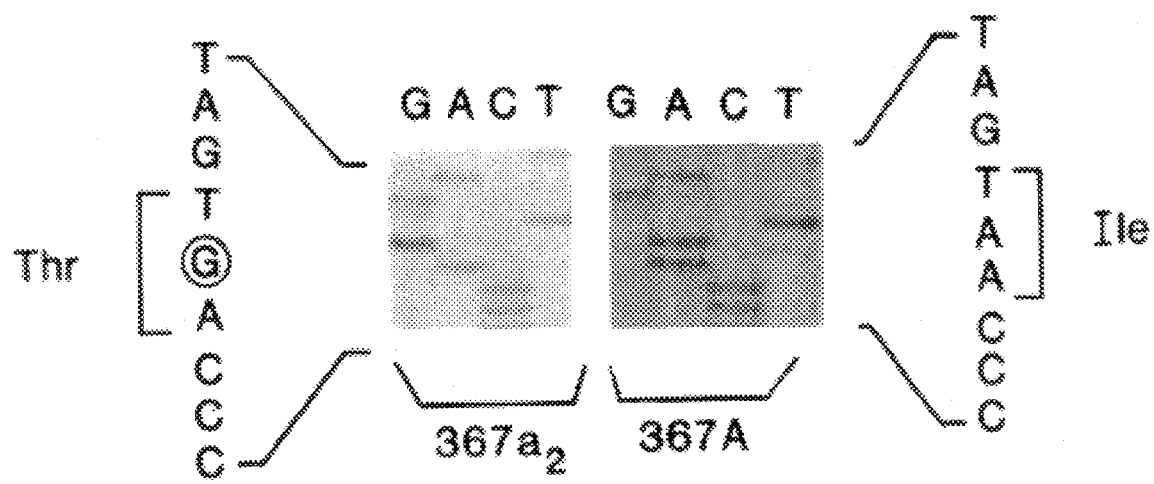
FIG. 5A represents the sequencing data showing maternal heterozygosity for a pathogenic mutation.

The maternal cDNA (cell line 367) was amplified by PCR in the 5' coding region between the NcoI and BstXI sites, subcloned, expressed and sequenced. As shown in FIG. 5A, DNA sequences were compared from DNA isolated from a colony containing normal maternal CBS cDNA (367A) and from another containing the abnormal allele ($367a_2$) also of maternal origin. The antisense strand symbol, Ⓖ, as shown in FIG. 5A, represents the sense-strand mutation T833C, confirming maternal origin of the I278T mutation in her son.

Figure 5B:
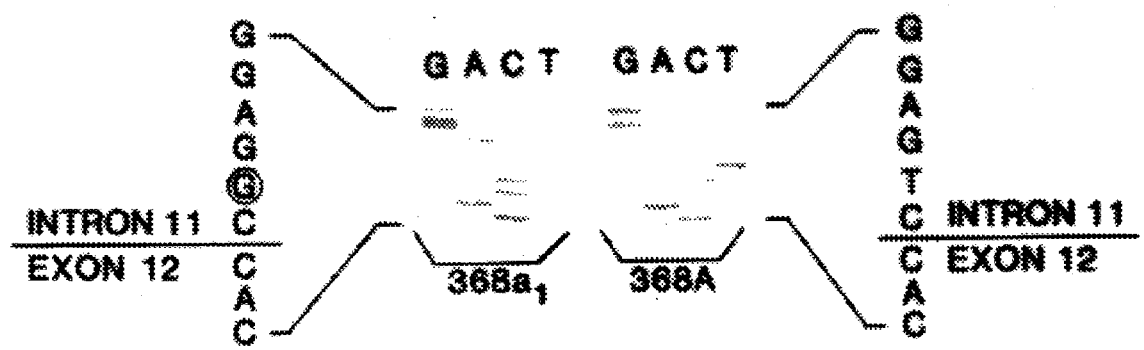
FIG. 5B represents the sequencing data showing paternal heterozygosity for a pathogenic mutation.

The suspicion of a splicing error led to sequencing the father's genomic DNA for intron 11 boundary mutations. Four of six clones sequenced contained an A to C transversion in the splice acceptor of intron 11 (FIG. 5B). The splice donor exhibited an apparently normal consensus sequence. These data explain the previously observed exon 12 deletion by misdirected splicing. In addition, paternal heterozygosity for this transversion is supported by the sequencing data.

Patient's father genomic DNA (800 ng), cell line 368, was amplified using primers ACGATCGATCGATGGTGTGC-CCA CAGGTGA (SEQ ID No:1) and CGTAGAATTCCT-GAGCGACAGGTGGATGC (SEQ ID No:2), upstream and downstream, respectively. The Eco RI and ClaI restricted PCR fragment was subcloned into a similarly prepared BlueScript vector (Stratagene) under conditions described in section D of Example 1. The 3' end of intron 11 and first 3 nucleotides of exon 12 in the antisense strand are shown in FIG. 5B: Ⓖ represents the sense strand mutation A→C in the consensus splice acceptor; 368A represents the wild type allele; and $368a_1$ represents the allele with mutation.

F. Western Analysis

Figure 6:
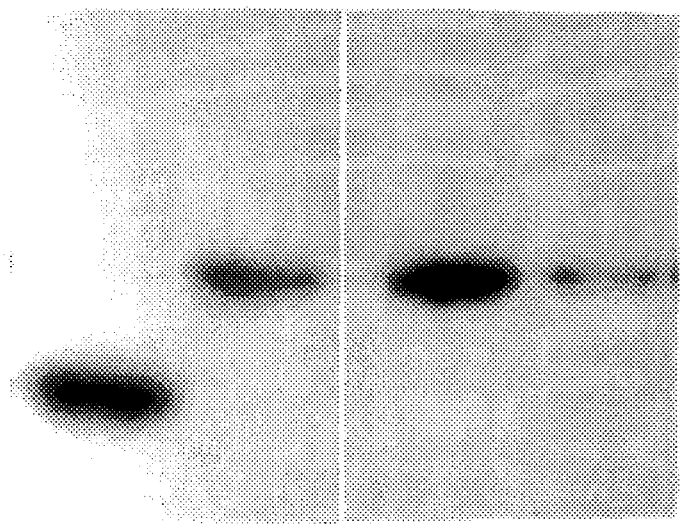
FIG. 6 represents a Western analysis of hybrid CBS expressed in *E. coli*.

To verify that CBS subunits were made in clones without catalytic activity, a Western analysis was performed on lysates of *E. coli* containing the hybrid CBS. The results of analysis are shown in FIG. 6. Lysates were prepared from bacteria expressing different hybrid constructs originating from each of patient 366's alleles. Vectors containing BK segments from each allele are represented in the left panel of FIG. 6 (250 µg bacterial protein). The right panel of FIG. 6 depicts CBS expressed by vectors containing the XB segments from each of the patient's alleles (500 µg bacterial protein). The capital A in FIG. 6 refers to regeneration of the normal, functional CBS subunit in the expression system. Symbols $a_1$ and $a_2$ in FIG. 6 refer to the deletion and substitution mutations found in the patient. CBS subunits were detected in all lysates, however, reduced amount of the immunoreactive material was found in the clones harboring plasmid with the I278T mutation. Clones expressing the shorter protein with deleted exon 12 yielded approximately as much immunoreactive material as the controls. These results suggest that the polypeptide containing I278T mutation is less stable than either the normal control or exon 12 deleted mutant protein in the *E. coli* system.

Modified Screening Expression System

The expression system for screening CBS mutations yielded sometimes false positive results derived from expressing uncut vectors that contained the complete normal CBS cDNA coding region. Therefore, to eliminate false positives, a modified screening expression system was used. This system introduces expression vectors, carrying a deletion in different segments of the CBS cDNA coding region, that express inactive forms of CBS.

The modified screening express system of the present invention involves the expression of different subregions of CBS cDNA from the patient after subcloning them into expression plasmids carrying the other two subregions of the normal CBS cDNA. The substitution of each cDNA subregion of the CBS coding region of the vector with the corresponding part derived from the patient was carried out by cutting out the vector's insert and substituting it with the same cDNA subregion coming from the patient. The hybrid vector-patient CBS was then expressed in *E. coli*. Inactive clones derived certainly from mutations present in the patient in that cDNA subregion of CBS. However, there was no way to determine if active clones contained subregions from patients with the normal CBS cDNA or uncut vectors still carrying the original insert, a complete normal CBS cDNA. To avoid these false positive results, three human CBS expression plasmids were prepared. All three plasmids were derived by deleting a segment from the pHCS3 plasmid. The segment was deleted in the subregion of the CBS coding region expected to be substituted by the corresponding subregion from patients' cDNA.

The presence of the deletion in each of the plasmids allowed a rapid screen for colonies carrying the expected insert. Subsequently, time required to find CBS mutations dramatically decreased. Moreover, the modified expression screening system insured a normal activity from CBS came from a wild type sequence in the patient and not from expression of an uncut vector containing the original insert.

Expression of E. coli clones containing the NX, BB or BK segments from patients' CBS cDNA showed about 50% of the NX and 50% of the BB clones to be inactive. All BK segments were normally active. Sequencing of inactive BB segments showed in all of them the presence of the E239K mutation. Sequencing of inactive NX segments showed the presence of two mutations segregating together on the same allele. Mutations were a C233G transversion, determining a Proline to Arginine change at position 78 of the protein (P78R), and a G307C transversion determining a Lysine to Asparagine substitution at position 102 of the amino acid chain. More likely these two linked mutations were inherited from the father. All the three siblings had the same genotype.

The C233G and the G307C mutations were both expressed independently in E. coli after having being reproduced independently by the in vitro mutagenesis system. Independently each of them decreased CBS activity by about 50% and when expressed together, CBS activity declined to zero.

CBS assay on fibroblasts showed an activity close to zero in all the three patients. According to these results, no CBS subunits from fibroblasts were detectable on Western blots. This was not true for the Western blot on E. coli lysates. CBS subunits were easily detectable, although decreased, in E. coli clones expressing either the three individual mutations or the linked pair. Taken together, these results show that the three patients were compound heterozygotes for three mutations and that their mother, apparently clinically unaffected, was homozygous for one of these mutations.

Method for Establishing Heterozygosity of an Individual

Mild Hyperhomocysteinemia (HHC) is a well established independent risk factor for premature occlusive arterial disease (POAD). Heterozygosity for CBS deficiency is considered as one of its causes. An examination was carried out of individual CBS alleles in four such patients who were previously described as heterozygotes for CBS deficiency.

An expression system was employed to functionally screen for pathogenic mutations in separated CBS alleles. The mRNA prepared from fibroblast cultures of four patients with HHC/POAD was reverse transcribed. The coding region of CBS cDNA was amplified by PCR and subcloned into bacterial vector pKK 388.1. CBS encoded by individual alleles was expressed in E. coli and assayed for activity.

The expression of the subcloned cDNAs revealed that at least seven independent alleles in four POAD/HHC patients encoded catalytically active and evidently stable CBS polypeptides.

Employing a molecular genetic approach, no pathogenic mutations were found in the coding region of CBS cDNA from seven independent alleles in POAD/HHC patients who had been considered heterozygotes. It appears the low CBS activity in fibroblasts of these patients is due to a diminished amount of catalytically unimpaired CBS polypeptides.

As a first step in detecting pathogenic mutations, CBS alleles of the four patients were separated by subcloning PCR amplified CBS cDNAs into a bacterial expression vector and the individual bacterial colonies were isolated. The coding region of CBS cDNAs was tested functionally for the presence of pathogenic mutations. The several bacterial colonies representative of each of the patient alleles were separately expressed and the CBS activity was assayed. The strategy to screen for pathogenic mutations in separated alleles is summarized in FIG. 8. An examination was made of at least seven independent alleles from four patients with POAD/HHC. The coding regions were examined functionally.

A. Screening for Inactive CBS Alleles among Patients with POAD/HHC

TABLE 2

Functional Screen For CBS Heterozygosity in Subcloned Human CBS cDNAs

| GROUP | CELL LINE# | FRACTION OF INACTIVE CLONES* | TOTAL FOR GROUP |
|---|---|---|---|
| CONTROLS | 2047 | 2/21 | 7% |
| | 2103 | 1/16 | |
| | 3077 | 1/17 | |
| PATIENTS WITH PREMATURE ARTERIAL DISEASE | 3014 | 2/16 | 12% |
| | 3022 | 2/16 | |
| | 3024 | 2/17 | |
| | 3030 | 2/17 | |
| OBLIGATORY HETEROZYGOTES FOR CBS DEFICIENCY | 367 | 4/18 | 31% |
| | 3056 | 5/18 | |
| | 3065 | 7/16 | |

Data were obtained from E. coli clones containing apparently normal sized CBS inserts $x^2$ test values for the differences between the three group of individuals: controls vs. obligatory heterozygotes 9.44 (p<0.005), controls vs. POAD/HHC 0.94 (p>0.05) and heterozygotes vs. POAD/HHC 6.17 (p<0.01)

An examination of Table 2 above shows that of 54 clones derived from three controls, only four (i.e. 7%) were found to be inactive in the expression system described earlier. These residual inactive clones were most probably still the result of PCR-induced artifacts. The number of inactive clones in controls, however, clearly differed from the values obtained in 3 obligate heterozygotes (31% clones were inactive, $x^2$=9.44, p<0.005). It was therefore reasonable to use these tests to assess the heterozygosity of patients with POAD/HHC. Expression of 66 clones derived from these 4 patients did not lead to a significantly elevated rate of inactive CBS colonies (12%) when compared with the controls ($x^2$=0.94, p>0.05). These functional data suggest that the group of POAD/HHC patients was not heterozygous for mutations in the coding region of the CBS gene which would affect enzyme activity, assuming that both parental alleles were equally represented in the clones which had been analyzed.

B. Segregation of CBS Activity with Allelic Polymorphisms

Examination of polymorphic markers in CBS cDNA permitted a test for the presence of the two parental alleles among clones exhibiting normal CBS activity. To carry out this test, clones were examined that were derived from obligate heterozygotes as well as the POAD/HHC patients who were informative for these polymorphisms. The results of these experiments are summarized in Table 3 below.

TABLE 3

Segregation of Synonymous Mutations with the Active Allele

| | | E.coli colonies with CBS activity | | |
|---|---|---|---|---|
| Obligatory heterozygotes | 3056 | 4 | 4 | inactive |
| | 3065 | 5 | inactive | 5 |
| PAD/HHC patients | 3014 | 7 | 2 | 5 |
| | 3022 | 8 | 2 | 6 |
| | 3030 | 8 | 3 | 5 |
| Controls | 2047 | 6 | 3 | 3 |
| | 3077 | 6 | 3 | 3 |

Individuals 3056, 3065, 3022, 3030, 2047 and 3077 were heterozygous for C699T (Tyr 233) synonymous mutation.

Individual 3014 was heterozygous for C1080T (Ala 360) synonymous mutation. Inactive represents an allele which contained the pathogenic mutation and yielded only inactive CBS clones.

Clones were first tested which produced active CBS in 2 obligate heterozygotes. Of the 4 active alleles tested for one patient (3056) all four exhibited "C" alleles (i.e. C699), indicating that this polymorphism segregated with active CBS for this individual. Similarly, all 5 clones examined for patient 3065 exhibited "T" alleles (T699). These results demonstrate that the PCR-based restriction fragment length polymorphism (RFLP) analytical method used clearly identifies the segregated parental alleles.

When the RFLP screening method was repeated employing appropriate polymorphisms (Table 3) on active cDNA clones derived from 3 patients with POAD/HHC, both parental alleles were found. While the alleles may not have been represented in equal proportion, their presence in active clones unequivocally demonstrates that both parental alleles encode enzyme which is catalytically functional under the conditions used for CBS assay. The fourth patient, 3024, did not exhibit these, or any other, polymorphisms.

The primary objective was to establish whether the abnormally depressed levels of CBS in POAD/HHC patients resulted from pathogenic mutations in the coding region of the gene. These mutations were not found in at least seven independent alleles derived from four unrelated patients and ruled out in at least three of these patients that they were heterozygous for CBS deficiency. Nevertheless, in one patient, 3024, the possibility remained that only one parental allele was examined while the other allele was deleted or yielded unstable mRNA.

The following examples are presented to illustrate the present invention and to assist one of ordinary skill in making and using the same. The examples are not intended in any way to otherwise limit the scope of the invention.

EXAMPLE 1

Method for Locating the Position of a Pathogenic Mutation

A. Human Cell Lines

Cultured skin fibroblasts from a control (2056), one CBS-deficient patient (366), and his mother (367) and father (368) were used. The patient is a mildly affected Ashkenazi Jewish male presently in his late twenties with dislocated lenses. He exhibits normal psychomotor developent. His homocystineimia and homocystinuria normalized after pyridoxine treatment despite the complete absence of CBS activity in his fibroblasts. Pulse experiments employing [$3^H$] leucine detected no CBS subunits following immunoprecipitation and SDS-PAGE in his fibroblast extracts. In vitro translation of the patient's and parental mRNAs, on the other hand, clearly revealed the patient's CBS subunits [Skovby et al., *Am J Hum Genet* 36:452–459 (1984)]. One, of apparently normal size, was inherited maternally; the other, much shorter, originated paternally.

B. Enzymes and DNA Modification

Restriction endonucleases were purchased from New England Biolabs. The 5' ends of restricted cloning cartridges were dephosphorylated with calf intestinal alkaline phosphatase (Boehringer Mannheim Corp.) according to the manufacturer's suggested procedure. Fragments of DNA were inserted into cartridges using $T_4$DNA ligase obtained from Promega following standard conditions [Ausubel et al., *Short Protocols in Molecular Biology*, Wiley, N.Y. (1989)]. When necessary, protruding 5' ends were made blunt by extending the 3' end with Klenow fragment DNA polymerase (Boehringer Mannheim Corp.) [Ausubel et al., *Short Protocols in Molecular Biology*, Wiley, N.Y. (1989)]. Taq DNA polymerase was purchased from Promega.

C. Normal Human CBS Expression Plasmid

Plasmid pKK 388.1 (Dr. J. Brosius, Columbia University, New York, N.Y.) was used for all expression experiments [Brosius, *Bio/Technology* 10:205–225 (1988)]. The polylinker Xma I site was destroyed after digestion by backfilling and religating. The coding region of the normal human liver CBS cDNA was amplified by PCR using primers P1 and P6. The product was phenol extracted, Centricon 100 purified [Tahara et al., *Bio Techniques* 8:366–368 (1990)], restricted with NcoI and KpnI, purified with Strataclean (Stratagene) and ligated into the NcoI/KpnI cut and dephosphorylated pKK 388.1 (Xma$^-$) vector. *E. coli* competent cells, DH5αF'IQ (BRL) were transformed with the expression plasmid designated pHCS3 (FIG. 2, top) and a single colony used for large plasmid preparation [Ausubel et al., *Short Protocols in Molecular Biology*, Wiley, N.Y. (1989)]. The complete circle at the top of FIG. 2 signifies the bacterial expression plasmid pHCS3, containing the entire coding region of human CBS cDNA.

D. Construction of Patient cDNA Screening Plasmids

Three expression cartridges were prepared by cutting the pHCS3 plasmid within the CBS coding region using the following pairs of restriction enzymes: NcoI/PmlI, XmaI/BstXI, and BstXI/KpnI for the NP, XB and BK cartridges, respectively (FIG. 2, bottom). Broken circles at the bottom of FIG. 2 represent the expression cartridges prepared to receive the appropriate patient cDNA inserts. $P_{trc}$ in FIG. 2 represents the trp/lac fusion promoter. HUCBS in FIG. 2 represents the full length coding region of human CBS cDNA. The dephosphorylated cartridges were gel purified (SeaKem GTG agarose, BRL) and recovered from the gel using glass beads (GeneClean, Bio 101).

To prepare patient cDNA inserts, fibroblast mRNAs were isolated as previously described [Skovby et al., *Am J Hum Genet* 36:452–459 (1984)]. First strand cDNAs were synthesized [Kraus et al, *Nucleic Acids Res* 13:942–952 (1985)] and portions of the cDNA were amplified by PCR as described previously [Tahara et al., *Bio Techniques* 8:366–368 (1990); Tahara et al., *Proc Natl Acad Sci USA* 87:1372–1376 (1990)].

The strategy for the preparation of inserts is depicted in FIG. 3 in the following manner. The long line represents CBS cDNA. The length of 250 base pairs is indicated by the length of the bar at the upper left of the figure. Restriction sites used for these preparations are indicated by the enzyme names. The initiation (1) and termination codons (1656) are represented by ATG and TGA, respectively. The open bars represent PCR products prepared with primers indicated by the black rectangles (P1 through P6). The primers used to prepare these fragments were:

A T C C C A C C A T G G G T T C T G A G A C - CCCCCAGGCAGAAGTG (SEQ ID No:3) (P1);

TACGATCGATTGTGAGAATTGGGGATTTCGTT (SEQ ID No:4) (P2);

CGTAGAATTCCCCTATGGTCAGAATCAACAAG (SEQ ID:5) (P3);

TACGATCGATCGTTGCTCTTGAACCATTG (SEQ ID No:6) (P4);

CGTAGAATTCAGTGGGCACGGGCGGCACCA (SEQ ID No:7) (P5);

TACGGGTACCAGCGCTCCGGACTTCACTTCTGG (SEQ ID No:8) (P6).

All sequences are read left to right from the 5' to the 3' ends. Underlines indicate artificial Nco I (P1) and Kpn I (P6) sites.

The two letter designations below each of the inserts refer to the enzyme pairs used to restrict the PCR fragments, indicated on the arrows in FIG. 3.

PCR products were phenol extracted, Centricon 100 purified [Tahara et al., *Bio Techniques* 8:366–368 (1990)], digested with the appropriate pairs of restriction endonucleases, then purified using Strataclean (Stratagene).

To complete the CBS expression plasmids, the purified cartridges and patient cDNA inserts were ligated as described earlier. Blunt end ligations were carried out in presence of 7.5% of polyethyleneglycol 8000. The transformed DH5αFTQ *E. coli* (BRL) were isolated on LB agar plates containing ampicillin. Both individual colonies and pools of colonies were used for expression experiments and DNA sequencing. Colonies were pooled to minimize the artifacts arising from misincorporation during PCR amplification of the target regions. Additionally, heterozygosity was readily apparent in the DNA sequences of the pools and subsequently could be verified in individual colonies.

Plasmid preparations were made using the dual SDS method [Ausubel et al., *Short Protocols in Molecular Biology*, Wiley, N.Y. (1989) ]. DNA sequences were determined by the dideoxy method [Sanger et al., *Proc Natl Acad Sci USA* 82: 7212–7216 (1977) ] using Sequenase 2.0 (USB).

E. Expression of CBS in *E. coli*

Bacterial cultures, 24 ml, were grown in SOB medium [Sambrook et al., *Molecular Cloning: A Laboratory Manual* 2nd ed., Vols 1–3, Cold Spring Harbor Laboratory Press, New York (1989)] to a turbidity of ~0.5 at 600 nm prior to induction with isopropyl-β-D-galactopyranoside (IPTG, BRL). Expression of CBS was induced for 1 h following addition of 0.33 mM IPTG. Cells were collected by centrifugation and washed once with phosphate buffered saline. The pellets were resuspended in 1 ml of 30 mM potassium phosphate (pH 6.0) then sonicated for 80 s at 50% duty cycle for 80 seconds with power setting of 3–4 in a ice/brine bath using a model W-225 sonicator (Heat-Ultrasonics Inc.). Cell lysates were cleared by centrifugation (14000×g for 10 minutes) and assayed for synthase activity or subjected to immunoprecipitation. CBS assays were performed essentially as described [Kraus, *Methods Enzymol* 143:388–394 (1987)], with some modifications. These modifications included limiting the amount of bacteria lysate in the assay and adding AdoMet to the reaction mixture. The incubation conditions for CBS in *E. coli* lysates were as follows: Tris-HCl (pH 8.6), 100 mM; serine, 2.5 mM; [$^{14}$C]-serine (~1500 cpm/nmol); homocysteine, 15 mM; BSA, 0.5 mg/ml; dithiothreitol, 1.5 mM; AdoMet, 0.5 mM; pyridoxal 5'-phosphate, 1 mM; and bacterial lysate, 20 μl (~100 ug of protein). The reaction was incubated for 4 hours at 37° C. in a total volume of 200 μl. Protein was determined according to Lowry [Lowry et al, *J Biol Chem* 393:265–275 (1951)]. Specific activity was expressed in units per mg protein (1 unit=1 nmol of cystathionine formed/hr).

For Western analysis, CBS was immunoprecipitated with rabbit antihuman CBS antibodies and *S. aureus* (Immunoprecipitin, BRL) [Kraus et al,*J Biol Chem* 258:7245–7248 (1983)]. The isolated CBS was subjected to SDS/PAGE and electroblotted onto a nitrocellulose membrane [Towbin et al., *Proc Natl Acad Sci USA* 76:4350–4354 (1979)]. Prior to use, the antiserum probes were preabsorbed with *E. coli* lysates to eliminate nonspecific cross reactivity [Sambrook et al., *Molecular Cloning: A Laboratory Manual* 2nd ed., Vols 1–3, Cold Spring Harbor Laboratory Press, New York (1989)]. The membrane was incubated in 5% nonfat dry milk, washed with PBS and incubated with the preabsorbed rabbit antirat CBS antibodies. To visualize the location of CBS, [$^{125}$I] Protein G was bound to the immunocomplexes followed by autoradiography of the blot at −80° C.

EXAMPLE 2

Modified Screening Expression System

The modified screening expression system was applied in studying a homocystinuric family. Among three affected siblings, the brother had a clinical phenotype totally different from that of his two sisters. The mother, expected to be a heterozygote for the disease, was a homozygote. Despite her homozygous deficiency of CBS, her clinical picture was perfectly normal, not showing any symptom typical of HCS.

Cultured skin fibroblasts from three affected HCS vitamin B6 responsive patients (a brother, cell line 1873, and two sisters, cell lines 1874, 1875) and from their mother (cell line 3009) were used. Clinical phenotypes of the brother and the two sisters differed significantly among each other. The sisters were mentally retarded, and suffered from osteoporosis and lens dislocations. The brother, whose diagnosis was made after the detection of the disease in his younger sisters, suffered only a calf thromboembolism at the age of 34. His mental development, skeletal system and lens status were normal. The mother didn't have any clinical feature typical of HCS but suffered from anemia and lung disease. All three patients were treated with vitamin B6 with resulting decrease of homocysteine in blood. Fibroblast CBS from both the mother and her offspring were assayed according according to the methods described in Kraus, *Methods Enzymol.* 143:388–394 (1987).

Preparation of both patients' and mother's mRNA and cDNA were carried out as described in section D of Example 1. In order to decrease the rate of Taq Polymerase artifacts, Deep Vent Polymerase (New England Biolabs) was used to amplify segments from patients' cDNA. PCR reactions (100 μl) contained 1 μl of cDNA, 1x Deep Vent buffer (10 mM KCl, 10 mM(NH$_4$)$_2$SO$_4$, 20 mM Tris-HCl pH 8.8, 0.1% Triton X-100), 300 μM of each dNTPs, 80 pmols of both sense and antisense primers and 3 mM MgSO$_4$. cDNA was subjected to hot start procedure and amplification was started after addiction of 1 U of Deep Vent Polymerase. Mother's full length cDNA (segment NK, NcoI/KpnI) was also prepared according to methods described in section C of Example 1.

Figure 7:
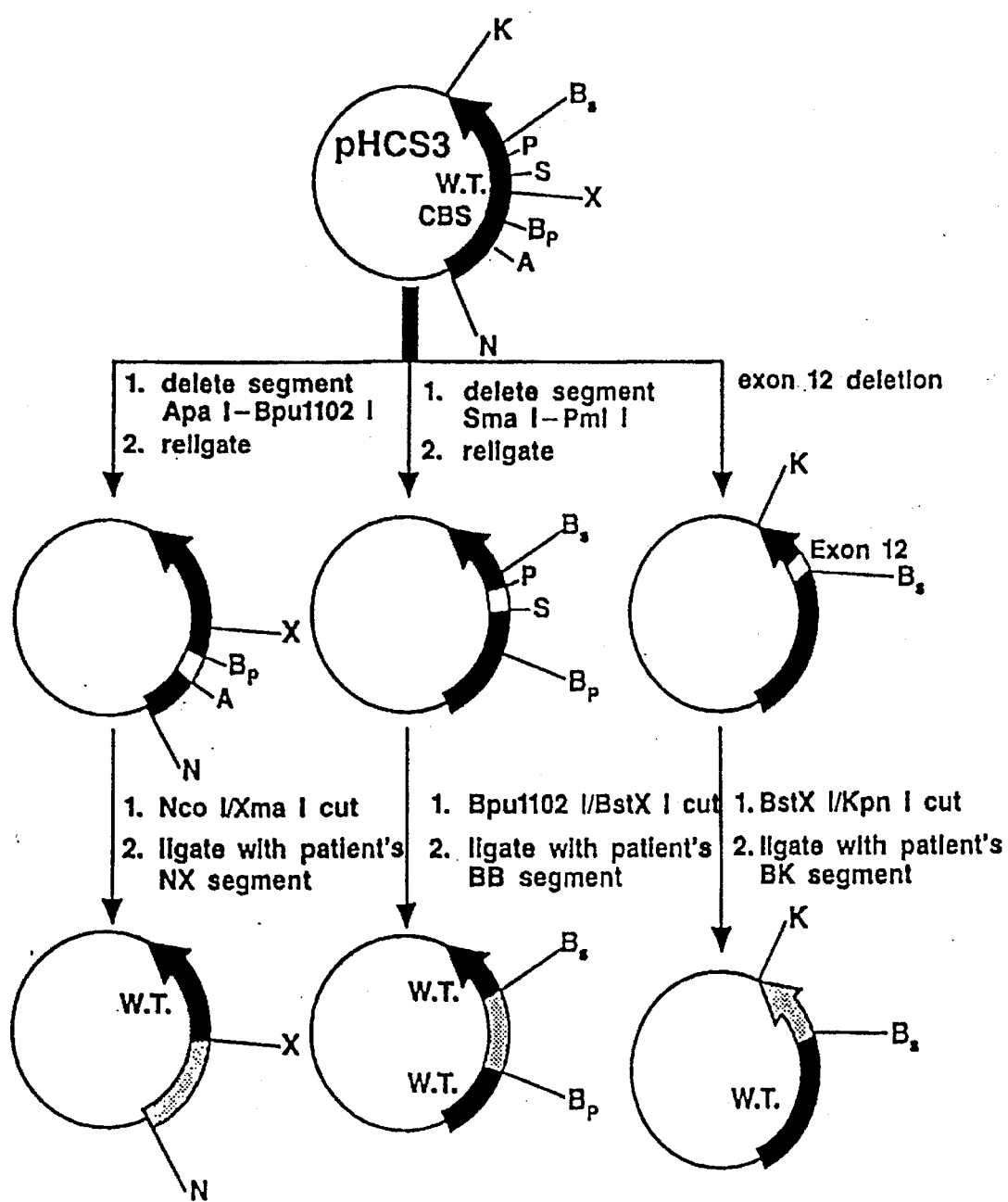
FIG. 7 is a schematic of the modified screening expression system showing the strategy in creating deletions in the expression vectors and in ligating each vector to the corresponding cDNA sequence from the patient.

Three human CBS expression plasmids were prepared for use in the modified screening expression system. All of them were derived from the pHSC3 plasmid prepared in section C of Example 1. Each of the three expression plasmids had a segment deleted within a CBS cDNA coding subregion expected to be substituted by the corresponding subregion from patients' cDNA. Enzymes used and sizes of deletions in each vector were: NX cartridge (for the NcoI/XmaI insert): Apa I/Bpu1102I deletion of 354 base pairs; BB cartridge (for the Bpu1102/BstXI insert): SmaI/PmlI deletion of 358 base pairs; BK cartridge (for the BstXI/KpnI insert) was already deleted of 135 bases deriving from a clone of the patient (366) missing exon 12 described in section A of Example 1. The deletions totally inactivated the three cartridges eliminating the problem of false positive assays. In addition, colonies of expression vectors could be screened by PCR after subcloning to confirm the presence of the patient's cDNA insert. This screening is based on the difference in size of the patient's cDNA insert from the corresponding subregion of the starting uncut expression vector that had a segment deleted. The complete strategy in creating deletions in the vectors and in ligating each vector to the corresponding fragment from the patient is described in FIG. 7. Transformation, *E. coli* expression, specific activity determination, and sequencing were all performed as described before in section E of Example 1.

To assess the relative contribution of each identified mutation in the CBS activity, an in vitro system of mutagenesis was developed to create each of them, separately, in the native cDNA. Each mutation was reproduced in vitro using three different PCRs. PCR conditions were the same as in section D of Example 1. The presence of each in vitro mutation in each expression plasmid was confirmed by sequencing. Mutations reproduced by the in vitro mutagenesis system were all expressed separately in the *E. coli* system.

Western blot analysis from both fibroblasts and *E. coli* of all three patients and their mother was performed as described in section E of Example 1.

EXAMPLE 3

Establishing Heterozygosity of an Individual

A. Patients and Cell Lines

Cell lines of POAD/HHC patients used for these studies have been described elsewhere [Boers et al., *N Engl J Med* 313:709–715 (1985); Clarke et al., *N Engl J Med* 324:1149–1155 (1991)] and are also summarized in Table I. Fibroblast cultures 2047, 2103 AND 3077 were derived from controls and cell lines 367, 3056 and 3065 originated from mothers of homocystinuric patients. Fibroblasts were culture in mem (Gibco BRL) with 10% fetal calf serum (Intergen), nonessential amino acids, glutamine, 100 U/ml of kanamycin and 100 ug/ml of streptomycin.

B. PCR Amplification of cDNA Using Pyrococcus sp. DNA Polymerase

DNA was also amplified using Pyrococcus sp. GB-D DNA polymerase (Deep Vent Polymerase, New England Biolabs) in lieu of the Taq enzyme. PCR reactions (100 l) contained 1 l of cDNA, 1× DeepVent buffer (NEB), 300M of each dNTPs, 80 pmols of both sense and antisense primers (described above), 4% dimethylsulfoxide and 8 mM MgSO$_4$ cDNA was subjected to the hot start PCR procedure as described above, using a Techne PHC-1 thermocycler with block temperature control. After adding 1 U of Psp polymerase to each tube, the temperature was cycled 30 times (96° C./1 min; 61° C., 1 min; 72° C., 2.3 min) to amplify target DNA.

C. Subcloning Strategy for Expression Experiments

Figure 8:
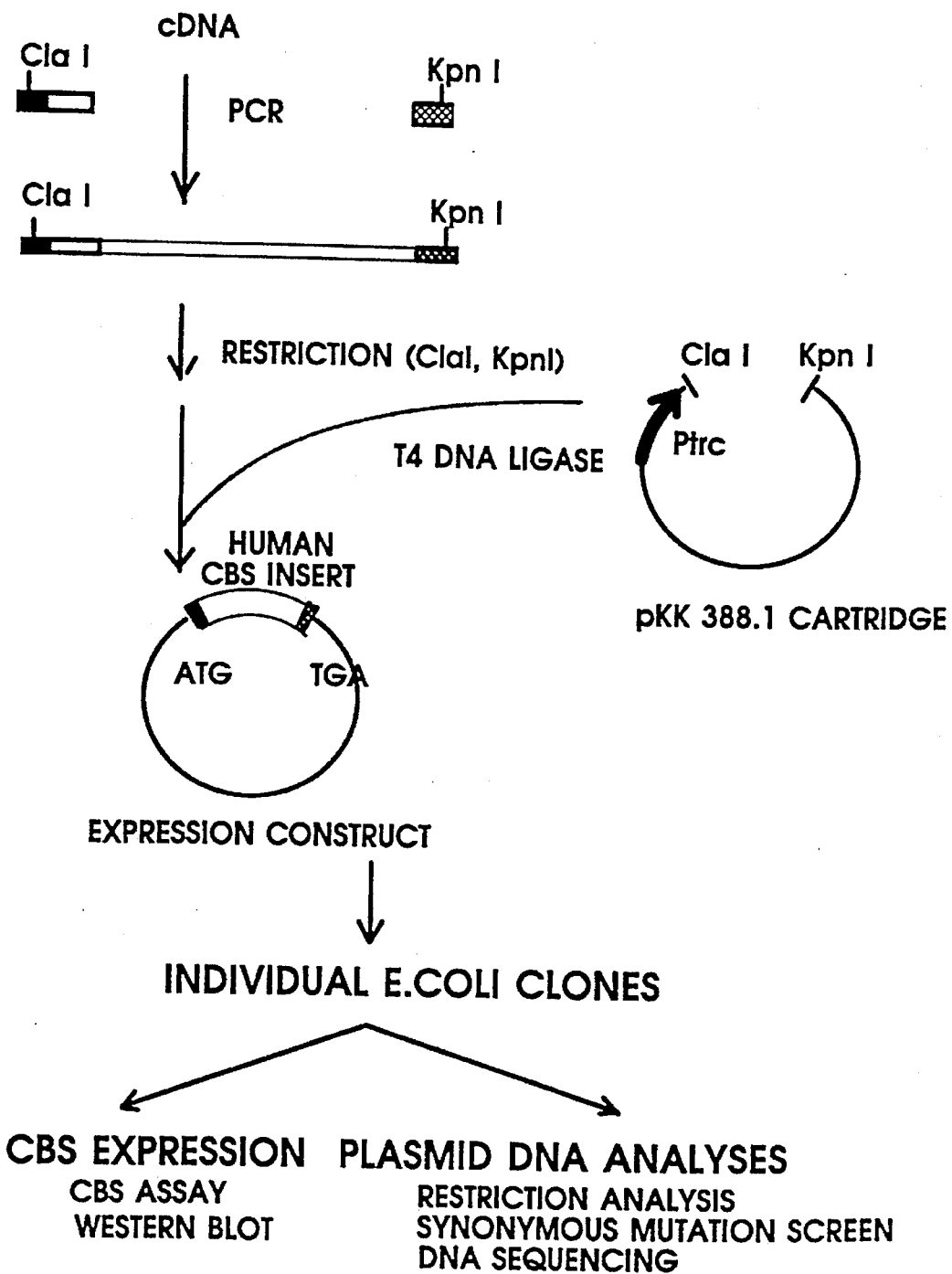
FIG. 8 is a schematic representing the strategy to screen for pathogenic mutations in separated CBS alleles.

The strategy for subcloning patient cDNA into a pKK 388.1 expression vector is depicted in FIG. 8. Plasmid pKK 388.1 ws restricted with ClaI and Kpn I (NEB), dephosphorylated with calf intestinal alkaline phosphatase (Boehringer), gel purified and recovered by electroelution [Ausubel et al., *Short Protocols in Molecular Biology*, p. 387, J Wiley & Sons, New York (1989)].

As shown in FIG. 8 patient cDNA was amplified by PCR using the appropriate pair of primers P1 and P2 (boxes) which contained artificial ClaI and KpnI sites, respectively. The PCR products were restricted with ClaI and KpnI, purified and ligated into pKK 388.1 cartridge. Resulting constructs contained cDNA sequence which was derived from tested individuals except of the small portion incorporated from P1 and P2 primers (shadowed boxes). The constructs were used for *E. coli* transformation and individual clones were isolated. CBS was expressed after induction with isopropyl-D-thiogalactopyranoside (IPTG), plasmid DNA of the clones was used for restriction analysis, sequencing or synonymous mutation screen.

PCR products were purified [Tahara et al., *BioTechniques* 8:366–368 (1990)] and restricted with ClaI and Kpn I. Restricted PCR products were gel purified and ligated in gel with the pKK cartridge using T$_4$ DNA ligase [Ausubel et al., *Short Protocols in Molecular Biology*, p. 387, J Wiley & sons, New York (1989)]. Expression constructs were used to transform DH5FTQ *E. coli* (Gibco,BRL) and individual, ampicillin-resistant colonies were subsequently used to express CBS or to prepare plasmid DNA. Expressed CBS was further examined by enzymatic assay or Western analysis while plasmid DNA was inspected by restriction analysis, synonymous mutations screen and DNA sequencing.

D. CBS Expression in *E. coli*

Individual clones harboring expression constructs with human cDNA inserts were incubated with IPTG to induce CBS synthesis; enzyme activity was measured in lysates of these cells as described [Koptsich and Kraus, *Human Mutation* 1:113–123 (1992)].

E. Screening for Synonymous Mutations

Two synonymous mutations in the coding region of CBS cDNA (C699T; T1080C) were screened by a PCR based RFLP method described below. Template DNAs for PCR (i.e. 200–500 ng of plasmid DNAs), 1 µl of cDNAs (prepared as described [Kraus et al., *Nucleic Acids Res.* 13:943–952 (1985)], 5 µl of bacterial cultures or a small amount of bacterial colonies, were mixed with 50 µl of water, denatured at 95° C. for 3 min (cDNA) or at 99° C. for 5 min (other templates) and rapidly chilled on ice.

The following were the conditions for PCR. Template preparations were mixed with appropriate pairs of oligonucleotide primers and other components as described previously [Tahara et al., *BioTechniques* 8:366–368 (1990)] using 2.5 U of Taq polymerase for each 100 µl reaction. The cycling was performed in a Hybaid thermal reactor under the following conditions: 30 cycles of denaturing at 94°C. for 1 min, annealing at 55° C. for 1 min and extension at 72°C. for 40 sec.

The screening for Y233Y synonymous mutation (699C/T) was accomplished in the following manner. The sense primer 5'-GACCAGTACCGCAACGCCAGCAACCCCC-TGGCTCAGTA-3' (SEQ ID No:9) contained at its 3' end one base pair mismatch (represented by the underlined G in place of C) that completed an RsaI site by incorporation of a C residue at the adjacent position 699. Accordingly, incorporation of a T in position 699 did not create this RsaI site. To monitor the efficiency of the digestion, another Rsa I site (underlined) was introduced into the antisense primer 5'-TTGTCCACCACCGTCCTGTCCAGTACCG-3' (SEQ ID No:10). Ten µl of PCR product were digested at 37° C. with 7 U of RsaI (NEB) in a total volume of 20 µl for 4 hours. These mixtures were subjected to agarose gel electrophoresis together with the uncut sample.

The screening for A360A synonymous mutation (1080C/T) was accomplished in the following manner. This screen was based on a restriction site polymorphism: nucleotide T in position 1080 was part of an FspI site while C in the same position produced an SfiI restriction site. The sense primer sequence was 5'-CGTAGAATTCAGTGGG-CACGGGCGGCACCA-3' (SEQ ID No:7) and the antisense oligonucleotide was 5'-TACGATCG-ATTCTGCAGCATCCACCTGTCCT-3' (SEQ ID No:11). Five µl of PCR reaction were digested for 4 hours with either 5 U of FspI (NEB) or 5 U of SfiI (NEB) at 37° C. in the total volume of 20 μl. Both digests were subsequently subjected to agarose gel electrophoresis.

Magic MiniPrep kits (Promega) were used to prepare plasmid DNA. Restriction endonucleases were purchased from NEB. DNA was sequenced by the dideoxy method [Sanger et al., *Proc Natl Acad Sci USA* 82:7212–7216 (1977)] using the CircumVent kit (NEB) and modified electrophoresis conditions [Krall, Lab Notes: *Common problems that inhibit successful seuencing in USB Comments* 19:64 (1992)].

Deposit of Strain Useful in Practicing the Invention

A deposit of biologically pure cultures of the following strain was made with the American Type Culture Collection, 12301 Parklawn Drive, Rockville, Md., the accession number indicated was assigned after successful viability testing, and the requisite fees were paid. Access to said culture will be available during pendency of the patent application to one determined by the Commissioner to be entitled thereto under 37 C.F.R. Section 1.14 and 35 U.S.C. Section 122. All restriction on availability of said culture to the public will be irrevocably removed upon the granting of a patent based upon the application and said culture will remain permanently available for a term of at least five years after the most recent request for the furnishing of a sample and in any case for a period of at least 30 years after the date of the deposit. Should the culture become nonviable or be inadvertently destroyed, it will be replaced with a viable culture(s) of the same taxonomic description.

The CBS cDNA sequence, inserted into the plasmid pHCS3 in the strain DH5αF'1Q *E. coli*, has been given ATCC No. 69370 and deposit date, Jul. 29, 1993.

The invention described herein provides a direct determination of sequence changes responsible for a genetically inherited disease rather than inference from linkage data. One use of the invention is for prenatal diagnosis to determine the presence of defective alleles. Another use is to detect the carriers of a defective allele. Such information helps evaluate the risk of passing on the disease and the severity of the disease to the carrier's offspring. In addition, the invention by identifying the types and locations of the mutations causing a disease can aid in determining the course of treatment for a patient suffering from the disease which can be a genetically inherited disease.

As will be apparent to those skilled in the art in which the invention is addressed, the present invention may be embodied in forms other than those specifically disclosed above without departing from the spirit or essential characteristics of the invention. The particular embodiments of the present invention described above, are, therefore, to be considered in all respects as illustrative and not restrictive. The scope of the present invention is as set forth in the appended claims rather than being limited to the examples contained in the foregoing description.

What is claimed is:

1. A method of locating the position of a pathogenic mutation in an enzyme gene of a human patient suffering from a disease, comprising the steps of:

(a) deleting at least one segment of a coding region of a normal enzyme cDNA in a starting expression vector to produce a vector containing an inactive enzyme sequence, wherein the segment deletion is within a subregion of the coding region of the normal cDNA corresponding to a subregion of a coding region of an enzyme cDNA from the patient;

(b) replacing in the vector containing the inactive enzymese the subregion of the normal cDNA having undergone the segment deletion with the inserted corresponding subregion of the patient enzyme cDNA to produce a hybrid enzyme;

(c) generating the hybrid enzyme from an expression system containing the expression vector, wherein the hybrid enzyme contains a portion encoded by at least one inserted subregion of the patient enzyme cDNA;

(d) assaying the hybrid enzyme for activity, an absence of enzyme activity or lower than normal enzyme activity of an enzyme generated from the normal enzyme cDNA indicating the presence of the pathogenic mutation in the inserted subregion of the patient enzyme cDNA;

(e) sequencing the inserted subregion of the patient enzyme cDNA in a total cDNA from the hybrid enzyme lacking activity or having lower than normal activity of the enzyme generated from the normal enzyme cDNA; and (f) comparing the inserted subregion of the patient enzyme cDNA with a corresponding subregion of the normal enzyme cDNA or a normal enzyme genomic DNA to locate the position of the pathogenic mutation.

2. The method of claim 1, wherein the disease is premature occlusive arterial disease.

3. The method of claim 1, wherein the disease is genetically inherited.

4. The method of claim 3, wherein the genetically inherited disease is homocystinuria.

5. The method of claim 1, wherein the enzyme is cystathionine β-synthase.

6. The method of claim 1, wherein the expression vector is a plasmid.

7. The method of claim 1, wherein the expression system is a prokaryotic or eukaryotic system.

8. The method of claim 7, wherein the prokaryotic system is *Escherichia coli*.

9. The method of claim 1, further comprises the screening of expression vectors from step (b) by PCR to confirm the presence 6f the patient's cDNA insert by comparing the difference in size of the patient's cDNA insert to a corresponding coding subregion having undergone segment deletion in the starting expression vector.

10. The method of claim 1, which further comprises identifying an enzyme allele in the expression vector by detecting a polymorphic marker for an allele.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

ACGATCGATC GATGGTGTGC CCACAGGTGA        30

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CGTAGAATTC CTGAGCGACA GGTGGATGC        29

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA -continued ( x i ) SEQUENCE DESCRIPTION: SEQ ID NO:3:

ATCCACCAT GGGTTCTGAG ACCCCCAGG CAGAAGTG       38

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TACGATCGAT TGTGAGAATT GGGGATTTCG TT       32

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CGTAGAATTC CCCTATGGTC AGAATCAACA AG       32

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

TACGATCGAT CGTTGCTCTT GAACCACTTG       30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGTAGAATTC AGTGGGCACG GGCGGCACCA       30

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

TACGGGTACC AGCGCTCCGG ACTTCACTTC TGG       33

-continued ( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

GACCAGTACC GCAACGCCAG CAACCCCTG GCTCAGTA 38

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TTGTCCACCA CCGTCCTGTC CAGTACCG 28

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

ATTCTGCAGC ATCCACCTGT CGCT 24